(12) United States Patent
Inoue

(10) Patent No.: US 11,299,707 B2
(45) Date of Patent: Apr. 12, 2022

(54) CULTURE MEDIUM PROTECTIVE LIQUID MATERIAL AND EMBRYO CULTURE METHOD

(71) Applicant: KITAZATO CORPORATION, Fuji (JP)

(72) Inventor: Futoshi Inoue, Fujinomiya (JP)

(73) Assignee: KITAZATO CORPORATION, Fuji (JP)

( * ) Notice: Subject to any disclaimer, the term of this patent is extended or adjusted under 35 U.S.C. 154(b) by 687 days.

(21) Appl. No.: 16/116,027

(22) Filed: Aug. 29, 2018

(65) Prior Publication Data

US 2019/0264170 A1  Aug. 29, 2019

(30) Foreign Application Priority Data

Feb. 23, 2018 (JP) .............................. JP2018-030754

(51) Int. Cl.
| | | |
|---|---|---|
| *C12N 5/00* | (2006.01) | |
| *C08L 91/08* | (2006.01) | |
| *C09K 3/10* | (2006.01) | |
| *C10M 175/02* | (2006.01) | |

(52) U.S. Cl.
CPC ............ *C12N 5/0012* (2013.01); *C08L 91/08* (2013.01); *C09K 3/1031* (2013.01); *C10M 175/02* (2013.01); *C12N 5/0018* (2013.01); *C08L 2555/72* (2013.01); *C09K 2003/1056* (2013.01); *C12N 2500/30* (2013.01); *C12N 2500/38* (2013.01)

(58) Field of Classification Search
CPC .............. C12N 5/0012; C12N 2500/30; C12N 2500/38; C12N 5/0018
See application file for complete search history.

(56) References Cited

U.S. PATENT DOCUMENTS

| | | | |
|---|---|---|---|
| 2018/0161380 A1* | 6/2018 | Munivar | ................ A61K 35/74 |
| 2021/0228530 A1* | 7/2021 | Hu | ........................ A61K 47/545 |

FOREIGN PATENT DOCUMENTS

| | | |
|---|---|---|
| JP | 2014-090691 A | 5/2014 |
| WO | 2016/154665 A1 | 10/2016 |

OTHER PUBLICATIONS

Paula-Lopes et al., "Manipulation of Antioxidant Status Fails to Improve Fertility of Lactating Cows or Survival of Heat-Shocked Embryos", Journal of Dairy Science, (Jul. 1, 2003), vol. 86, Issue 7, pp. 2343-2351.

Office Action (Notice of Reasons for Refusal) dated Dec. 14, 2021, by the Japanese Patent Office in corresponding Japanese Patent Application No. 2018-030754 and an English Translation of the Office Action. (8 pages).

* cited by examiner

*Primary Examiner* — Robert D Harlan
(74) *Attorney, Agent, or Firm* — Buchanan Ingersoll & Rooney PC

(57) ABSTRACT

A culture medium protective liquid material of the present invention covers a culture medium when a living cell is cultured. The culture medium protective liquid material contains liquid paraffin which is liquid at room temperature as a main component thereof and an antioxidative substance for restraining the liquid paraffin from being oxidized.

21 Claims, No Drawings

CULTURE MEDIUM PROTECTIVE LIQUID MATERIAL AND EMBRYO CULTURE METHOD

BACKGROUND OF THE INVENTION

Field of the Invention

The present invention relates to a culture medium protective liquid material which covers a culture medium when a living cell is cultured (more specifically, when an embryo is cultured) and an embryo culture method using the same.

Description of the Related Art

In culturing living cells, more specifically, in culturing embryos, it has been common to replace a plurality of kinds of culture mediums every other day or every few days in conformity to a development stage of an embryo. Recently a single step culture medium method of culturing embryos for a consecutive few days without replacing culture mediums has come to be used.

In the above-described single step culture medium method, embryos are cultured by dispensing a culture medium in the shape of a flat plate into a container (in other word, dispensing a culture medium into a container in layer form), covering upper surfaces of the dispensed culture mediums with a culture medium protective liquid material (more specifically, mineral oil), and putting the embryos into the respective culture mediums covered with the mineral oil.

According to another common method, embryos are cultured by dispensing the culture medium in the shape of a droplet to a bottom surface of a container, covering the dispensed culture mediums with mineral oil, and putting the embryos into the respective culture mediums covered with the mineral oil (Japanese Patent Application Publication No. 2014-90691).

By covering the culture mediums each having the embryo therein with the mineral oil, it is possible to avoid the moisture content of each culture medium from evaporating and stabilize the pH, osmotic pressure, and configuration (more specifically, droplet-shaped) thereof.

But when the embryos are cultured consecutively without replacing culture mediums or the mineral oil, it is difficult to maintain the quality of the mineral oil. The deterioration of the mineral oil causes an embryo-culturing environment to deteriorate and may result in the extinction of the embryos.

It is an object of the present invention to provide a culture medium protective liquid material (mineral oil) which can be restrained from being deteriorating in quality so that the culture medium protective liquid material is capable of maintaining a living cell-culturing environment properly.

SUMMARY OF THE INVENTION

The culture medium protective liquid material which achieves the above-described object of the present invention has the following form:

The culture medium protective liquid material of the present invention covers a culture medium when a living cell is cultured. The culture medium protective liquid material contains liquid paraffin which is liquid at room temperature as a main component thereof and an antioxidative substance for restraining the liquid paraffin from being oxidized.

DESCRIPTION OF THE PREFERRED EMBODIMENTS

The culture medium protective liquid material of the present invention is described below with reference to embodiments.

The culture medium protective liquid material of the present invention is used to cover a culture medium when a living cell is cultured. The culture medium protective liquid material contains liquid paraffin which is liquid at room temperature as a main component thereof and an antioxidative substance for restraining the liquid paraffin from being oxidized.

The culture medium protective liquid material of the present invention covers the culture medium when a living cell is cultured (more specifically, when an embryo is cultured), restrains the water content of the culture medium from evaporating, stabilizes the pH and osmotic pressure of the culture medium, and maintains its original configuration when the culture medium protective liquid material is at a droplet-shaped embryo culture medium.

As the liquid paraffin, a mixture of hydrocarbon compounds which are liquid at room temperature (25 degrees C.) and which have 12 to 35 carbon atoms is preferably used. It is preferable that the hydrocarbon compounds consist of saturated hydrocarbon compounds. It is preferable that the culture medium protective liquid material, in other words, the liquid paraffin does not substantially contain aromatic hydrocarbons or sulfur compounds. The culture medium protective liquid material is preferable free of aromatic hydrocarbons and free of sulfur compounds. As the liquid paraffin, it is possible to use both soft liquid paraffin and heavy liquid paraffin.

It is favorable that the liquid paraffin has an average molecular weight of 200 to 500 and especially favorable that the liquid paraffin has the average molecular weight of 250 to 450. It is favorable that the liquid paraffin has a kinematic viscosity of 7 to 45 $mm^2/s$ at 40 degrees C. and especially favorable that the liquid paraffin has the kinematic viscosity of 8 to 42 $mm^2/s$ at 40 degrees C. It is favorable that the liquid paraffin has a specific gravity of 0.82 to 0.89.

More specifically, it is favorable that the soft liquid paraffin has an average molecular weight of 270 to 330, a kinematic viscosity of 5-15 $mm^2/s$ at 40 degrees C., and a specific gravity of 0.820 to 0.845. It is favorable that the heavy liquid paraffin has an average molecular weight of 400 to 450, a kinematic viscosity of 35-45 $mm^2/s$ at 40 degrees C., and a specific gravity of 0.855 to 0.890.

The culture method in which the culture medium protective liquid material of the present invention is used is not limited to the above-described single step culture medium method, but it is possible to use the culture medium protective liquid material of the present invention in other culture methods. As the form of an embryo culture medium in which the culture medium protective liquid material of the present invention is used, it is possible to use both a droplet method (microdrop method) method and a flat plate method (lamination method, overlay method).

In the microdrop method, embryos are cultured by preparing droplet-shaped culture mediums on a bottom surface of a container (for example, dish), covering exposed surfaces of the culture mediums with the culture medium protective liquid material of the present invention, and holding the embryos in the respective droplet-shaped culture mediums. In the flat plate method, embryos are cultured by dispensing a culture medium in the shape of a flat plate to an entire bottom surface of a container, laminating the culture medium protective liquid material of the present invention on exposed upper surfaces of dispensed culture mediums to cover the upper surfaces of the respective culture mediums therewith, and holding the embryos in the respective flat plate-shaped culture mediums.

In a case where the culture medium protective liquid material of the present invention is an embryo culture medium protective liquid material which covers surfaces of droplet-shaped culture mediums each holding a living cell, in other words, in a case where the culture medium protective liquid material of the present invention is used in the microdrop method, it is preferable to use the culture medium protective liquid material as the liquid paraffin having an average molecular weight of 400 to 450, a kinematic viscosity of 35 to 45 $mm^2/s$ at 40 degrees C., and a specific gravity of 0.855 to 0.890.

In a case where the culture medium protective liquid material of the present invention is an embryo culture medium protective liquid material which covers surfaces of culture mediums dispensed in the shape of a flat plate to the bottom surface of the container, in other words, in a case where the culture medium protective liquid material of the present invention is used in the flat plate method (lamination method, overlay method), it is preferable to use the culture medium protective liquid material as the liquid paraffin having an average molecular weight of 270 to 330, a kinematic viscosity of 5 to 15 $mm^2/s$ at 40 degrees C., and a specific gravity of 0.820 to 0.845.

The culture medium protective liquid material of the present invention contains the antioxidative substance, added to the liquid paraffin which is the main component thereof, which has an antioxidative action for restraining the liquid paraffin from being oxidized. As the antioxidative substance, at least one kind of substance selected from among the following substances is preferable: vitamin E, derivatives of the vitamin E, vitamin C, derivatives of the vitamin C, lycopene, vitamin A family, carotenoids, vitamin B, derivatives of the vitamin B, flavonoids, glutathione, selenium, uric acid, melatonin, urobilinogen, and polyphenol. Not less than two kinds of the antioxidative substances selected from among the above-described ones may be added to the liquid paraffin.

The antioxidative substances oil-soluble (fat-soluble) and lipophilic are preferable. As oil-soluble vitamin, vitamin A family, provitamin A family, vitamin E, derivatives of the vitamin E, derivatives of oil-soluble vitamin B, and derivatives of oil-soluble vitamin C are exemplified. As the antioxidative substance, the vitamin E and the derivatives of the vitamin E are preferable. Tocopherol and tocopherol acetate are also preferable.

As the vitamin E or the derivatives of the vitamin E, the following substances are preferable: tocopherol such as α-tocopherol, β-tocopherol, γ-tocopherol, δ-tocopherol, DL-α-tocopherol, D-δ-tocopherol; and the derivatives of the vitamin E such as acetate DL-α-tocopherol, succinate DL-α-tocopherol, DL-α-tocopherol calcium, DL-α-tocopherol nicotinate, and DL-α-tocopherol linoleate.

As the vitamin C, ascorbic acid is preferable. As the derivatives of the vitamin C, derivatives of oil-soluble vitamin C such as L-ascorbyl tetra-2-hexyldecanoate, ascorbyl stearate, ascorbyl palmitate, ascorbyl dipalmitate, and ascorbyl tetraisostearate are preferable.

As the vitamin A family, retinol, retinal (vitamin A1), dehydroretinal (vitamin A2), carotene, and lycopene (provitamin A) are exemplified. As the carotenoids, carotene, lycopene, fucoxanthin, astaxanthin, lutein, zeaxanthin, and β-cryptoxanthin are exemplified.

As the vitamin B or the derivatives of the vitamin B, thiamine hydrochloride, thiamine sulfate (vitamin B1), vitamin B2 (riboflavin), niacin (nicotinic acid, nicotinic acid amide), pantothenic acid, vitamin B6 (pyridoxine, pyridoxal, and pyridoxamine), and vitamin B12 (cyanocobalamin) are exemplified.

As the flavonoids, flavone, isoflavone, flavonol, flavanone, flavanonol, catechin, auron, anthocyanidin, chalcone, and dihydrochalcone are exemplified.

The amount (content) of the antioxidative substance of the culture medium protective liquid material of the present invention to be added to 100 parts by weight of the liquid paraffin is set to favorably 0.001 to 0.1 parts by weight and especially favorably 0.005 to 0.05 parts by weight. The culture medium protective liquid material of the present invention is prepared by adding a predetermined amount of the antioxidative substance to the liquid paraffin and sufficiently stirring the mixture thereof. The culture medium protective liquid material can be also prepared by adding a predetermined amount of the antioxidative substance to a small amount of the liquid paraffin to prepare liquid paraffin containing the antioxidative substance at a high concentration, adding the liquid paraffin containing the antioxidative substance at a high concentration to a remaining amount of the liquid paraffin, and stirring the mixture thereof.

The embryo culture method of the present invention is described below with reference to embodiments.

The embryo culture method of this invention comprises a step of dispensing a culture medium into a container (for example, dish) in a layer form, a step of putting an embryo (preferably, embryos) into the culture medium, a step of covering with a culture medium protective liquid material to an exposed surface of the culture medium including the embryo, a step of culturing the embryo in the culture medium covered with the culture medium protective liquid material.

As the culture medium protective liquid material, the above-mentioned culture medium protective liquid material can be used.

The culture medium protective liquid material contains liquid paraffin which is liquid at room temperature as a main component thereof and an antioxidative substance for restraining the liquid paraffin from being oxidized.

The antioxidative substance is preferably vitamin E, the culture medium protective liquid material is preferably free of aromatic hydrocarbons and free of sulfur compounds. An amount of the antioxidative substance to be added to 100 parts by weight of the liquid paraffin is preferably 0.005 to 0.1 parts by weight. The liquid paraffin has preferably an average molecular weight of 270 to 330, a kinematic viscosity of 5-15 $mm^2/s$ at 40 degrees C., and a specific gravity of 0.82 to 0.85.

Another embryo culture method of this invention comprises a step of forming a droplet-shaped culture medium (preferably, plurality of droplet-shaped culture mediums) on a bottom surface of a container (for example, dish), a step of putting an embryo (preferably, embryos) into the droplet-shaped culture medium, a step of covering with a culture medium protective liquid material to an exposed surface of the droplet-shaped culture medium including the embryo, a step of culturing the embryo in the culture medium covered with the culture medium protective liquid material.

As the culture medium protective liquid material, the above-mentioned culture medium protective liquid material can be used.

The culture medium protective liquid material contains liquid paraffin which is liquid at room temperature as a main component thereof and an antioxidative substance for restraining the liquid paraffin from being oxidized.

The antioxidative substance is preferably vitamin E, the culture medium protective liquid material is preferably free of aromatic hydrocarbons and free of sulfur compounds. An amount of the antioxidative substance to be added to 100 parts by weight of the liquid paraffin is preferably 0.005 to 0.1 parts by weight. The liquid paraffin has preferably an average molecular weight of 400 to 450, a kinematic viscosity of 35 to 45 $mm^2/s$ at 40 degrees C., and a specific gravity of 0.85 to 0.88.

The examples of the present invention are described below.

Example 1

0.01 parts by weight of vitamin E was added to 100 parts by weight of liquid paraffin [specific gravity: 0.838, kinematic viscosity: 9.976 $mm^2/s$ (40 degrees C.), average molecular weight: 300 and, pour point: −12.5 degrees C. These specifications conform to the Japanese Pharmacopoeia]. Thereafter the mixture was sufficiently stirred to prepare culture medium protective liquid material of the present invention.

Example 2

0.01 parts by weight of vitamin E was added to 100 parts by weight of liquid paraffin [specific gravity: 0.861, kinematic viscosity: 39.30 $mm^2/s$ (40 degrees C.), average molecular weight: 430, and pour point: −12.5 degrees C. These specifications conform to the Japanese Pharmacopoeia]. Thereafter the mixture was sufficiently stirred to prepare culture medium protective liquid material of the present invention.

Comparison Example 1

The liquid paraffin [specific gravity: 0.838, kinematic viscosity: 9.976 $mm^2/s$ (40 degrees C.), average molecular weight: 300, and pour point: −12.5 degrees C. These specifications conform to the Japanese Pharmacopoeia] was used as culture medium protective liquid material of the comparison example 1.

Experiment 1

As a culture medium, Human Tubal Fluid (HTF) having the following formulation was prepared:

The content of the HTF is as follows: 2.04 mM of calcium chloride dihydrate, 5.06 mM of potassium chloride, 0.37 mM of potassium dihydrogen phosphate, 0.2 mM of magnesium sulfate heptahydrate, 110.37 mM of sodium chloride, 148.33 mM of sodium hydrogen carbonate, 2.78 mM of dextrose, 21.4 mM of DL-sodium lactate, 0.33 mM of sodium pyruvate, and 1.19 mM of HEPES.

As experimental cells, early mouse embryos (B6C3F1× B6D2F1) were prepared.

After a culture medium was dispensed in the shape of a flat plate to a petri dish, 93 early mouse embryos (B6C3F1× B6D2F1) were moved to respective embryo culture media. Thereafter exposed surfaces of a part of the embryo culture media each holding the early mouse embryo were covered with the culture medium protective liquid material of the example 1. Exposed surfaces of a remaining part of the embryo culture media were covered with the culture medium protective liquid material of the comparison example 1. After the embryos were cultured for zero hour (immediately after the exposed surfaces of the respective embryo culture media were covered with the culture medium protective liquid material), 24 hours, and 96 hours from the time when the exposed surfaces of the respective embryo culture media were covered with the culture medium protective liquid material of the example 1 and that of the comparison example 1, the culture medium protective liquid material was collected to conduct an endotoxin test, a sulfuric acid color reaction test, and a POV (peroxide value) test. A biological test was also conducted to check an embryonic development ratio.

After the embryos were cultured for zero hour and 24 hours by using the culture medium protective liquid material of the comparison example 1, the culture medium protective liquid material was collected to conduct the endotoxin test, the sulfuric acid color reaction test, and the POV test. As a result, it was found that the amount of the endotoxin was not more than 0.001EU of the detection limit value, that no reaction was shown in the sulfuric acid color reaction test, and that the POV was not more than 0.1 meq/kg of the detection limit value. After the embryos were cultured for 96 hours by using the culture medium protective liquid material of the comparison example 1, the culture medium protective liquid material was collected to conduct the above-described tests. As a result, it was found that the amount of the endotoxin was not more than 0.001EU of the detection limit value and that no reaction was shown in the sulfuric acid color reaction test. Thus, the results found in the endotoxin test and the sulfuric acid color reaction test were the same as those found after the embryos were cultured for zero hour and 24 hours. But the POV of the culture medium protective liquid material was 0.3 meq/kg which was higher than the POV thereof found when the embryos were cultured for zero hour and 24 hours. It was also found in the biological test that the cleavage ratio of the mouse embryo was 93.5% (87/93) and that the blastocyst development ratio was 87.0% (81/93).

After the embryos were cultured for zero hour, 24 hours, and 96 hours by using the culture medium protective liquid material of the example 1, the culture medium protective liquid material was collected to conduct the endotoxin test, the sulfuric acid color reaction test, and the POV test. As a result, it was found that the amount of the endotoxin was not more than 0.001EU of the detection limit value, that no reaction was shown in the sulfuric acid color reaction test, and that the POV was not more than 0.1 meq/kg of the detection limit value. It was also found that in the biological test, the cleavage ratio of the mouse embryo was 100% (93/93) and that the blastocyst development ratio was 100% (93/93). These results indicate that the culture medium protective liquid material of the example 1 was significantly higher ($P<0.01$) than the culture medium protective liquid material of the comparison example 1 in both the cleavage ratio of the mouse embryo and the blastocyst development ratio. Thus, the embryonic development ratio of the mouse embryo measured in the case where the culture medium protective liquid material of the example 1 was used was higher ($P<0.01$) than the embryonic development ratio of the mouse embryo measured in the case where the culture medium protective liquid material of the comparison example 1 was used.

Experiment 2

The same culture medium and experimental cells as those of the experiment 1 were used in the experiment 2.

After a plurality of droplet-shaped culture mediums were formed on a bottom surface of a petri dish, 50 early mouse embryos were put into the respective culture mediums. Exposed surfaces of the droplet-shaped culture mediums were covered with the culture medium protective liquid material of the example 2 to culture the early mouse embryos. After the early mouse embryos were cultured for zero hour, 24 hours, and 96 hours by using the culture medium protective liquid material of the example 2, the culture medium protective liquid material was collected to conduct the endotoxin test, the sulfuric acid color reaction test, and the POV test. As a result, it was found that the amount of the endotoxin was not more than 0.001EU of the detection limit value, that no reaction was shown in the sulfuric acid color reaction test, and that the POV was not more than 0.1 meq/kg of the detection limit value. It was also found that in the biological test, the cleavage ratio of the early mouse embryos was 100% (50/50) and that the blastocyst development ratio was 100% (50/50).

The culture medium protective liquid material of the present invention has the following form:

(1) The culture medium protective liquid material of the present invention is used to cover the culture medium when a living cell is cultured. The culture medium protective liquid material contains the liquid paraffin which is liquid at room temperature as the main component thereof and the antioxidative substance for restraining the liquid paraffin from being oxidized.

The culture medium protective liquid material of the present invention covers the culture medium when the living cell is cultured, thereby restraining the water content of the culture medium from evaporating, stabilizing the pH and osmotic pressure of the culture medium, preventing the liquid paraffin from deteriorating in its quality during consecutive culture, and restraining the quality of the mineral oil from deteriorating due to denaturation of the liquid paraffin. Thereby the culture medium protective liquid material of the present invention enables a good living cell culture environment to be maintained.

The above-described embodiment may have the following form:

(2) A culture medium protective liquid material according to the above (1), which does not substantially contain aromatic hydrocarbons or sulfur compounds.
(3) A culture medium protective liquid material according to the above (1) or (2), wherein said antioxidative substance is at least one kind of substance selected from among vitamin E, derivatives of said vitamin E, vitamin C, derivatives of said vitamin C, lycopene, a vitamin A family, carotenoids, vitamin B, derivatives of said vitamin B, flavonoids, glutathione, selenium, uric acid, melatonin, urobilinogen, and polyphenol.
(4) A culture medium protective liquid material according to the above (1), which covers an exposed surface of a culture medium covering an embryo which is a living cell.
(5) A culture medium protective liquid material according to the above (1), wherein an amount of said antioxidative substance to be added to 100 parts by weight of said liquid paraffin is 0.005 to 0.1 parts by weight.
(6) A culture medium protective liquid material according to the above (1), wherein said liquid paraffin has an average molecular weight of 200 to 500.
(7) A culture medium protective liquid material according to the above (1), wherein said liquid paraffin has a kinematic viscosity of 8 to 45 mm$^2$/s at 40 degrees C.
(8) A culture medium protective liquid material according to the above (1), wherein said liquid paraffin has a specific gravity of 0.82 to 0.89.
(9) A culture medium protective liquid material according to the above (1), wherein said liquid paraffin has an average molecular weight of 270 to 330, a kinematic viscosity of 5-15 mm$^2$/s at 40 degrees C., and a specific gravity of 0.820 to 0.845.
(10) A culture medium protective liquid material according to the above (1), wherein said liquid paraffin has an average molecular weight of 400 to 450, a kinematic viscosity of 35-45 mm$^2$/s at 40 degrees C., and a specific gravity of 0.855 to 0.890.
(11) A culture medium protective liquid material according to the above (1), which covers surfaces of culture mediums dispensed into a container (for example, dish), wherein said liquid paraffin has an average molecular weight of 270 to 330, a kinematic viscosity of 5-15 mm$^2$/s at 40 degrees C., and a specific gravity of 0.82 to 0.85.
(12) A culture medium protective liquid material according to the above (1), which covers surfaces of culture mediums each covering an embryo which is a living cell, wherein said liquid paraffin has an average molecular weight of 400 to 450, a kinematic viscosity of 35 to 45 mm$^2$/s at 40 degrees C., and a specific gravity of 0.85 to 0.88.

What is claimed is:

1. A culture medium protective liquid material for covering a culture medium when a living cell is cultured, said culture medium protective liquid material containing liquid paraffin which is liquid at room temperature and an antioxidative substance for restraining said liquid paraffin from being oxidized.

2. A culture medium protective liquid material according to claim 1, which does not substantially contain aromatic hydrocarbons or sulfur compounds.

3. A culture medium protective liquid material according to claim 1, wherein said antioxidative substance is at least one kind of substance selected from among vitamin E, derivatives of said vitamin E, vitamin C, derivatives of said vitamin C, lycopene, a vitamin A family, carotenoids, vitamin B, derivatives of said vitamin B, flavonoids, glutathione, selenium, uric acid, melatonin, urobilinogen, and polyphenol.

4. A culture medium protective liquid material according to claim 1, which covers an exposed surface of a culture medium covering an embryo which is a living cell.

5. A culture medium protective liquid material according to claim 1, wherein an amount of said antioxidative substance to be added to 100 parts by weight of said liquid paraffin is 0.005 to 0.1 parts by weight.

6. A culture medium protective liquid material according to claim 1, wherein said liquid paraffin has an average molecular weight of 200 to 500.

7. A culture medium protective liquid material according to claim 1, wherein said liquid paraffin has a kinematic viscosity of 8 to 45 mm$^2$/s at 40 degrees C.

8. A culture medium protective liquid material according to claim 1, wherein said liquid paraffin has a specific gravity of 0.82 to 0.89.

9. A culture medium protective liquid material according to claim 1, wherein said liquid paraffin has an average molecular weight of 270 to 330, a kinematic viscosity of 5-15 mm$^2$/s at 40 degrees C., and a specific gravity of 0.820 to 0.845.

10. A culture medium protective liquid material according to claim 1, wherein said liquid paraffin has an average molecular weight of 400 to 450, a kinematic viscosity of 35-45 mm$^2$/s at 40 degrees C., and a specific gravity of 0.855 to 0.890.

11. A culture medium protective liquid material according to claim 1, which covers surfaces of culture mediums dispensed to a container,
wherein said liquid paraffin has an average molecular weight of 270 to 330, a kinematic viscosity of 5-15 mm$^2$/s at 40 degrees C., and a specific gravity of 0.82 to 0.85.

12. A culture medium protective liquid material according to claim 1, which covers surfaces of culture mediums each covering an embryo which is a living cell,
wherein said liquid paraffin has an average molecular weight of 400 to 450, a kinematic viscosity of 35 to 45 mm$^2$/s at 40 degrees C., and a specific gravity of 0.85 to 0.88.

13. A culture medium protective liquid material according to claim 1, wherein said antioxidative substance is vitamin E, said culture medium protective liquid material is free of aromatic hydrocarbons and free of sulfur compounds, an amount of said antioxidative substance to be added to 100 parts by weight of said liquid paraffin is 0.005 to 0.1 parts by weight, and said liquid paraffin has an average molecular weight of 270 to 330, a kinematic viscosity of 5-15 mm$^2$/s at 40 degrees C., and a specific gravity of 0.820 to 0.845.

14. A culture medium protective liquid material according to claim 1, wherein said antioxidative substance is vitamin E, said culture medium protective liquid material is free of aromatic hydrocarbons and free of sulfur compounds, an amount of said antioxidative substance to be added to 100 parts by weight of said liquid paraffin is 0.005 to 0.1 parts by weight, and said liquid paraffin has an average molecular weight of 400 to 450, a kinematic viscosity of 35-45 mm$^2$/s at 40 degrees C., and a specific gravity of 0.855 to 0.890.

15. The culture medium protective liquid material according to claim 1, wherein the amount of liquid paraffin in the culture medium protective liquid material is greater than the amount of antioxidative substance.

16. A culture medium protective liquid material for covering a culture medium when a living cell is cultured, said culture medium protective liquid material containing liquid paraffin which is liquid at room temperature and an antioxidative substance for restraining said liquid paraffin from being oxidized, said culture medium protective liquid material does not substantially contain aromatic hydrocarbons or sulfur compounds.

17. The culture medium protective liquid material according to claim 16, wherein the amount of said antioxidative substance to be added to 100 parts by weight of said liquid paraffin is 0.005 to 0.1 parts by weight.

18. The culture medium protective liquid material according to claim 16, wherein said antioxidative substance is at least one kind of substance selected from among vitamin E, derivatives of said vitamin E, vitamin C, derivatives of said vitamin C, lycopene, a vitamin A family, carotenoids, vitamin B, derivatives of said vitamin B, flavonoids, glutathione, selenium, uric acid, melatonin, urobilinogen, and polyphenol.

19. A culture medium protective liquid material covering a culture medium, said culture medium protective liquid material containing liquid paraffin which is liquid at room temperature and an antioxidative substance for restraining said liquid paraffin from being oxidized, said culture medium protective liquid material covering an exposed surface of a culture medium covering an embryo, the embryo being a living cell that is being cultured.

20. A culture medium protective liquid material covering a culture medium according to claim 19, wherein the amount of said antioxidative substance to be added to 100 parts by weight of said liquid paraffin is 0.005 to 0.1 parts by weight.

21. A culture medium protective liquid material covering a culture medium according to claim 19, wherein said antioxidative substance is at least one kind of substance selected from among vitamin E, derivatives of said vitamin E, vitamin C, derivatives of said vitamin C, lycopene, a vitamin A family, carotenoids, vitamin B, derivatives of said vitamin B, flavonoids, glutathione, selenium, uric acid, melatonin, urobilinogen, and polyphenol.

* * * * *